United States Patent [19]
Bral

[11] Patent Number: 5,429,145
[45] Date of Patent: Jul. 4, 1995

[54] MEANS FOR SIMULTANEOUSLY BRUSHING AND/OR FLOSSING INTERPROXIMAL AREAS IN AN ARCH

[76] Inventor: Pourang Bral, 82-13 258 St., Floral Park, N.Y. 11004

[21] Appl. No.: 939,608

[22] Filed: Sep. 2, 1992

[51] Int. Cl.⁶ .............................................. A61C 15/00
[52] U.S. Cl. ................................................... 132/323
[58] Field of Search .............................. 433/6, 80, 141; 132/323, 324, 325, 326, 327; 15/167.1

[56] References Cited

U.S. PATENT DOCUMENTS

| | | | |
|---|---|---|---|
| 3,319,626 | 5/1967 | Lindsay | 433/6 X |
| 4,531,530 | 7/1985 | Aiken | 132/323 |
| 4,729,392 | 3/1988 | Tenny | 132/323 |
| 5,022,417 | 6/1991 | Cimini | 132/323 |
| 5,101,843 | 4/1992 | Peng | 132/323 |
| 5,163,840 | 11/1992 | Bourke | 433/6 |

*Primary Examiner*—Nicholas D. Lucchesi

[57] ABSTRACT

A custom made mouthpiece for individual patients, used for flossing and/or brushing the interproximal areas between two or more teeth in a dental arch which has as an option, a gum massaging device to massage the gums either simultaneously or not simultaneously with brushing and/or flossing of interproximal areas.

18 Claims, 3 Drawing Sheets

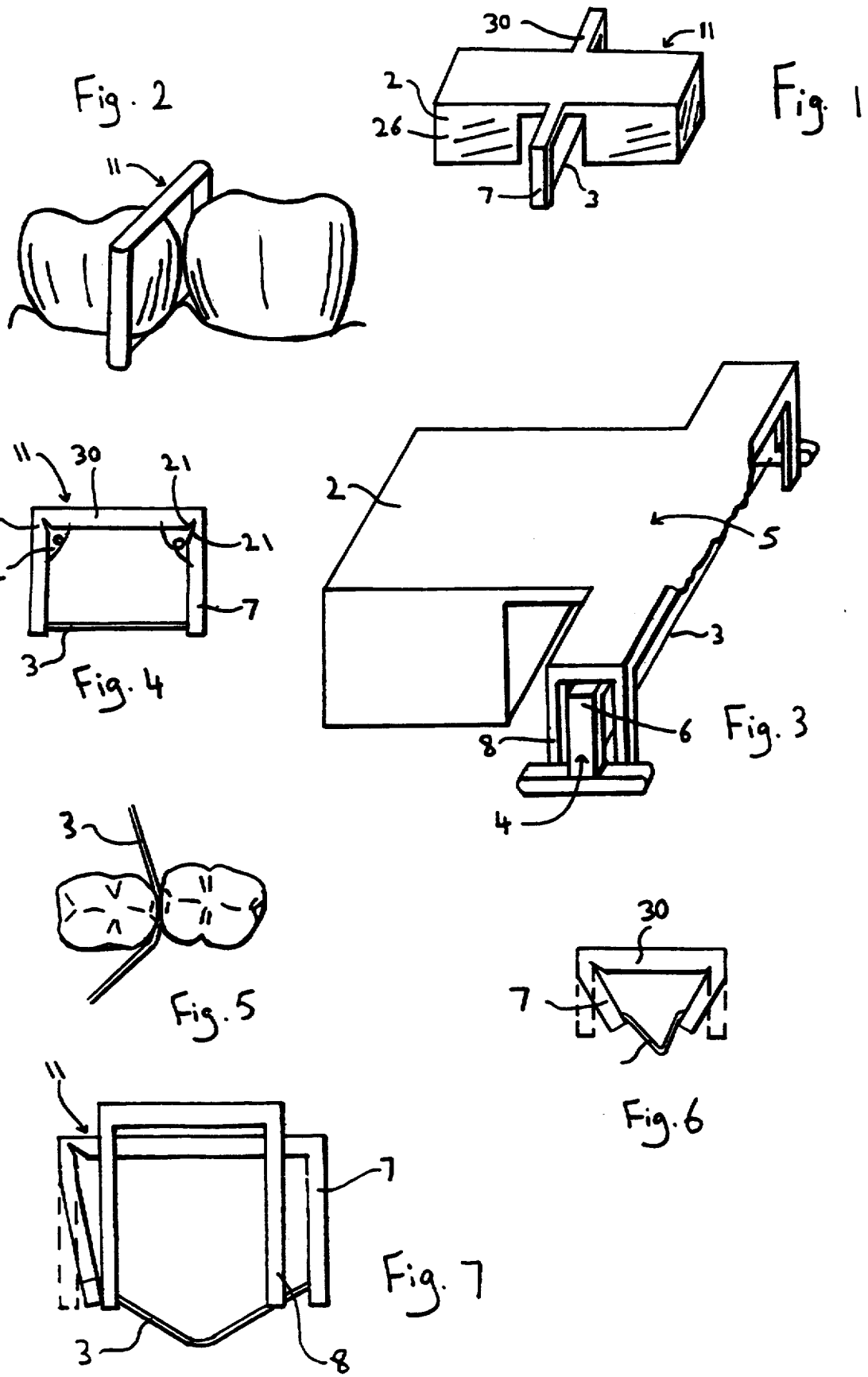

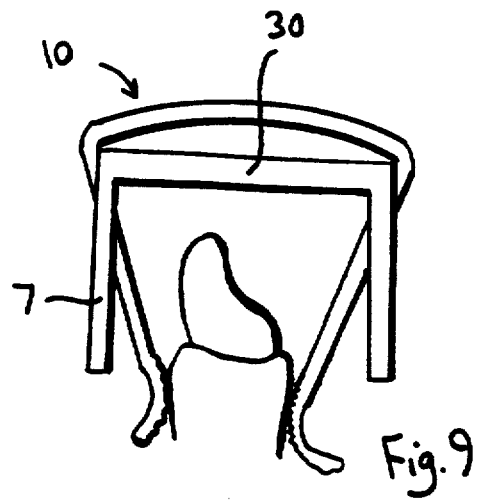
Fig. 9
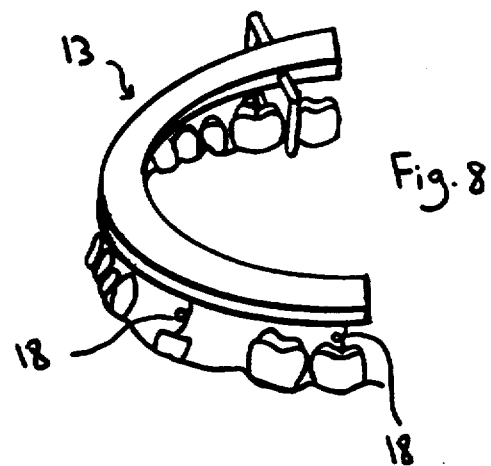
Fig. 8
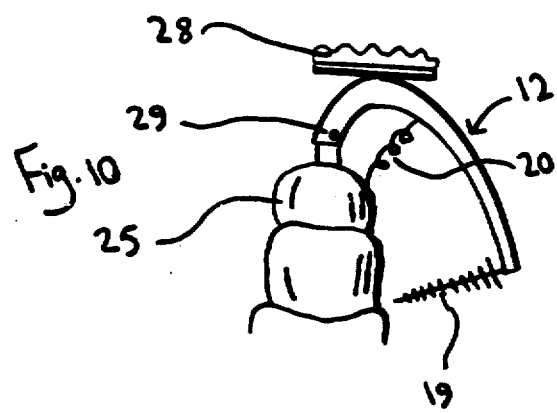
Fig. 10
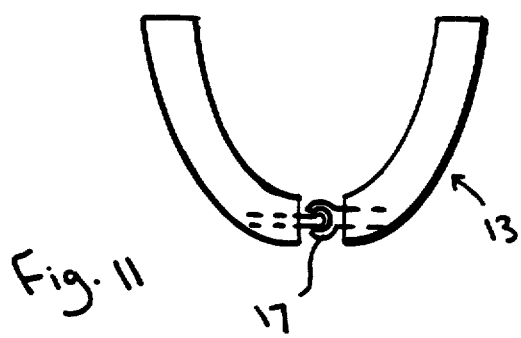
Fig. 11
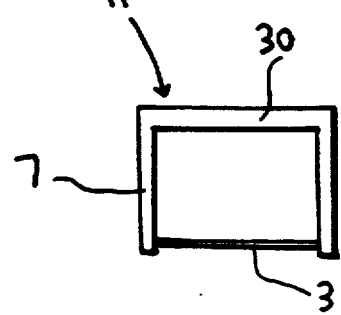
Fig. 13
Fig. 14
Fig. 12

MEANS FOR SIMULTANEOUSLY BRUSHING AND/OR FLOSSING INTERPROXIMAL AREAS IN AN ARCH

BACKGROUND OF THE INVENTION

The present invention relates generally to oral hygiene and more particularly to interproximal brushing and/or flossing and still more particularly to a custom made mouthpiece for interproximal brushing and/or flossing for simultaneously brushing and/or flossing a plurality of interproximal areas in a dental arch.

SUMMARY OF THE INVENTION

Disclosed in this invention is a custom made mouthpiece used for flossing and/or brushing interproximal areas between two or more teeth in a dental arch. Said mouthpiece, including at least one mechanically actuated lever for interproximal brushing and/or one mainframe for flossing the interproximal areas, and a material such as wax or resin to connect said mechanically actuated lever(s) and/or said mainframe(s) together and hold them in proper position with respect to the dental arch of the patients, is customized to fit the particular arrangement, size, and shape of the teeth of individual patients.

OBJECTS OF THE INVENTION

It is an object of this invention to disclose a new and useful mouthpiece used to floss and/or brush the interproximal areas of two or more teeth in one dental arch simultaneously.

It is another object of this invention to disclose a new and useful device which provides easy access to hard-to-reach interproximal areas of the dentition for flossing and/or brushing said interproximal areas.

It is another object of this invention to disclose a new and useful device which requires little or no skill or manual dexterity for flossing and/or brushing interproximal areas of the dentition.

It is another object of this invention to disclose a new and useful device which provides an easy alternative to flossing with plain flossing thread and with individual flossing-thread guiders, and/or to brushing with interproximal brushes; and therefore being instrumental in encouraging otherwise non-cooperative patients to attend to their dental hygiene needs.

It is another object of this invention to disclose a new and useful device for flossing and/or brushing one or more interproximal areas of the dentition which is guided by the movement of the mandible and/or by moving a handle which is connected to said device and which extends out of the mouth for easy manipulation.

It is another object of this invention to disclose a new and useful device for flossing and/or brushing one or more interproximal areas of the dentition which can easily enter and exit the mouth by using a Flexible or bendable material, such as a hinge in its construction.

It is another object of this invention to disclose a new and useful device for flossing and/or brushing one or more interproximal areas of the dentition which has replaceable brushes.

It is another object of this invention to disclose a new and useful device for flossing and/or brushing one or more interproximal areas of the dentition which has replaceable mainframes.

It is another object of this invention to disclose a new and useful device for flossing and/or brushing one or more interproximal areas of the dentition which is easier to guide into the interproximal area and also wraps around the tooth better for more effective flossing.

It is another object of this invention to disclose a new and useful device for flossing and/or brushing one or more interproximal areas of the dentition which comprises a mechanically actuated lever which enters and exits interproximal areas by opening and closing the mouth.

DESCRIPTION OF THE DRAWING

FIG. 1 illustrates a mainframe with two lateral extensions.

FIG. 2 illustrates a mainframe in an interproximal area.

FIG. 3 illustrates a receptacle with replaceable mainframe so as to enable one to replace flossing threads after wear.

FIG. 4 illustrates a mainframe with flossing thread along with different parts of said mainframe.

FIG. 5 illustrates a flossing thread in interproximal area of two adjacent teeth, viewed from occlusal aspect.

FIG. 6 illustrates how arms move if pulling of adequate force is applied to the flossing thread.

FIG. 7 illustrates how a mainframe with flexible corners reacts to a pulling at the flossing thread until the arm reaches a guidance member blocking further inward movement.

FIG. 8 illustrates how certain springs may push the custom made mouthpiece away from the teeth and the gingiva.

FIG. 9 illustrates a cross section of the mandible in the incisor region along with a gum massaging device.

FIG. 10 illustrates a mechanically actuated lever situated on a mandibular molar viewed mesially.

FIG. 11 illustrates how a hinge can help the mouthpiece in entering and exiting the mouth more easily.

FIG. 12 illustrates how the position of flossing thread affects proper flossing, viewed occlusally.

FIG. 13 illustrates a mainframe with an elongate member supporting two arms which hold a flossing thread.

FIG. 14 illustrates a facial view of two adjacent posterior teeth.

DESCRIPTION OF PREFERRED EMBODIMENTS

Figure 15:
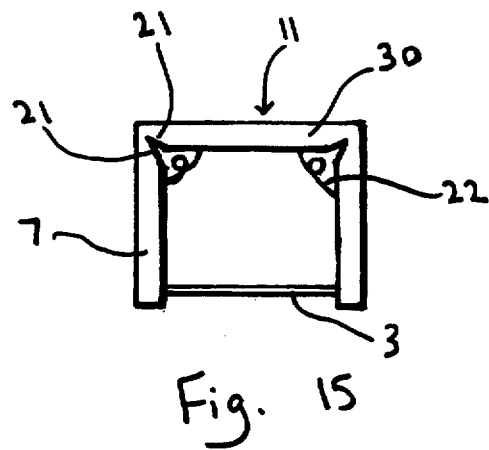
FIG. 15 illustrates a mainframe with hinderance blocks.
Figure 16:
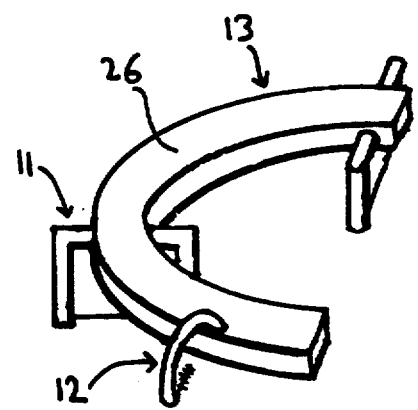
FIG. 16 illustrates a custom made mouthpiece containing mainframes and mechanically actuated levers.

The preferred embodiments of the invention are illustrated with reference to FIGS. 1-17.

The mouthpiece 13 disclosed herein facilitates flossing of teeth and cleaning of interproximal areas. Said mouthpiece 13 is custom made to fit the dental arch(es) of each individual patient. It cleans the interproximal areas of two or more teeth in one arch at the same time. Said mouthpiece 13 includes at least one or more mainframes, 11, and/or one or more mechanically actuated levers, 12, as in FIG. 16.

A diagram of said mainframe, 11, is presented in FIG. 1. Said mainframe 11 includes at least an elongate member 30 supporting at least two arms 7 which project from said elongate member 30 in a generally upright manner towards generally the same direction and which retain a flossing thread 3 in a position away from said elongate member 30 a) by a distance equal to or greater than the height of a clinical crown of a tooth of a specific size, and b) so that said clinical crown of said tooth can loosely fit between said arms 7, said mainframe(s) 11 held firmly in position by a material 26 that has an initial soften state so as to enable one to place said mainframe(s) 11 on one's dental arch so that said flossing thread 3 retained by each said mainframe 11 be located between two adjacent teeth. In a specific design of the invention, a lateral extension, 2, contains said material, 26, which is at some time soft. Said material, 26, can be made, for example, of wax which is softened by adequate heating, or of a resin that is soft until cured chemically, by heat, or by visible or U.V. light. The purpose of said lateral extension, 2, is to retain the proper position of said mainframe, 11, with respect to the dental arch of the patient and/or to provide adhesion—or otherwise connection—of two or more said mainframes, 11, together. Many examples of the design of said mainframe, 11, can be easily thought of. In one specific design of the invention, FIG. 3, use is made of a replaceable mainframe, 4, which can separably be fastened to a receptacle, 5 so that preferably said replaceable mainframe, 4, has limited or no movement with respect to said receptacle, 5. One or more said lateral extensions, 2, may accompany said receptacle, 5. However, only one said lateral extension, 2, is demonstrated here for clarity. In one specific design of the invention, said mainframe, 11, or said replaceable mainframe, 4, provides a tension on said flossing thread, 3. Said mainframe, 11, or said replaceable mainframe, 4, provides such tension on said flossing thread, 3, preferably, both by being flexible at at least one place along the body of said mainframe, 11, or said replaceable mainframe, 4—for example at corners, 6; and by pushing said arms, 7, of said mainframe, 11, or said replaceable mainframe, 4, outward as indicated by arrows through a springy outward movement, as in FIG. 4. As FIG. 6 suggests, since said mainframe, 11, or said replaceable mainframe, 4, is flexible at least at one place—e.g.; at said corners, 6; any pulling of adequate force at said flossing thread, 3, will move inward at least one of said arms,7. In a specific design of the invention, this inward movement of said arm(s), 7, does not go unchecked since a guidance member, 8, of said receptacle, 5, stops said inward movement at a certain point as in FIG. 7. Said guidance member 8 projects from said receptacle 5 so that it is positioned in the path of the inward movement of said arm 7 and stops said movement at a point along the path of said movement of said arm 7. Therefore, said flossing thread, 3, after wrapping around an individual tooth, has enough tension to disrupt plaque and debris in interproximal areas. The hinderance of said movement can be accomplished through more than one means. Another example of such hinderance of said movement—besides the example mentioned above involving said guidance member, 8—is illustrated as in FIG. 15. At least at one said corner, 6—or any other place along the body of said replaceable mainframe, 4, or said mainframe, 11—there is at least one flexible area so that at least one portion of said arm 7 of said mainframe 4 is moveable and/or rotatable at least in an inwardly-outwardly fashion with respect to at least another part of said mainframe 4.

In a specific design of the invention, the inwardly movement and/or rotation of said arm 7 is limited by at least two blocking bodies 21, at least one on each side of said flexible area, and facing each other in such a way that at least in one position in the path of movement of said arm(s) 7 of said mainframe 4, at least two of said blocking bodies 21 facing each other come in contact and oppose further inwardly movement of said moveable arm(s) 7 of said mainframe 4. In a specific design of the invention, said rotatable and/or moveable arm 7 is pushed outwardly by a spring 22 with respect to the rest of said replaceable mainframe 4.

A diagram of said mechanically actuated lever, 12, is illustrated in FIG. 10.

Said mechanically actuated lever 12 rotates around a pivot 29 which is held firmly in position in said mouthpiece 13. Each said mechanically actuated lever 12 holding and guiding upon actuation from generally the lingual or the facial direction at least one brush 19 into at least one interproximal area to which said mechanically actuated lever 12 is designated. Said mechanically actuated lever(s) 12 are held firmly in position by said material 26 that is at some time soft, so as to enable one to place said mechanically actuated lever(s) 12 positioned on one's dental arch so that said mechanically actuated lever(s) 12 be kept in such a position that each said mechanically actuated lever 12 guide upon actuation at least one said brush 19 into at least one interproximal area from generally the facial or the lingual direction. Said mechanically actuated lever, 12, is fastened to at least one said brush, 19, that can clean the interproximal area. In a specific design of the invention, said brush, 19, is driven by said mechanically actuated lever 12 into and out of the interproximal area from generally the facial or lingual direction. In a specific design of the invention, said brush, 19, is replaceably fastened to said mechanically actuated lever 12. In a specific design of the inventions, said mechanically actuated lever, 12, includes at least one adjusting means, 25—which is, for example, made of said material, 26, whose functions include at least one or more of the following: A. Adjusting to the height and size of various teeth. Since the position, shape, and size of each interproximal area with respect to the teeth and the dental arch of the patient is very likely to be different from those of another interproximal area, and since when mass manufactured, said mechanically actuated levers 12 come in a limited number of sizes, said adjusting means, 25, is helpful in positioning said brush, 19, such that it will easily enter and exit the interproximal area. B. In a specific design of the invention, in which an action such as opening and closing of the mouth, or the movement of and the pressure exerted by hand, induces said mechanically actuated lever 12 to drive said brush, 19, in and out of the interproximal area, a pressor, 28, is used to transfer the force exerted by the opposite arch to said mechanically actuated level 12. Since the position, shape, and size of the teeth on the opposite arch are different from tooth to tooth—and teeth might even be lacking, said adjusting means, 25, is used to fit said pressor, 28, to the hard and soft tissue of the opposite arch. And C. Said adjusting means, 25—especially if made of wax or resin or the like—can be used to adhere, or otherwise connect, said mechanically actuated lever, 12, to at least another said mechanically actuated lever, 12, or to at least another said mainframe, 11. In a specific design of the invention, said adjusting means, 25, adheres, or otherwise connects, said pressor, 28, to another member in order to control the actuation of said mechanically actuated lever, 12; said member can for example be a rod extended out of the mouth enabling one to manually actuate said mechanically actuated lever, 12. Said mechanically actuated lever 12 can have a variety of designs. A preferred design of said mechanically actuated lever 12 is illustrated in FIG. 10. In this design, said pressor, 28, transfers the force exerted by the opposite arch, by hand, or by other means, to said mechanically actuated lever 12. Said mechanically actuated level 12 is curved away from said pressor, 28, near where it turns around said pivot, 29. Said pressor, 28, pushes said mechanically actuated lever 12 towards the dental arch on which said mechanically actuated lever, 12, is or can be positioned. With the right amount of force exerted on it, said mechanically actuated lever 12 turns around said pivot, 29, and drives said brush, 19, into an interproximal area. In a specific design of the invention, when the force exerted on said pressor, 28, is removed, a spring, 20, returns said mechanically actuated lever 12 to its original position , and drives said brush, 19, out of the interproximal area. A custom made mouthpiece, 13, includes at least one or more said mainframes, 11, and/or one or more said mechanically actuated levers, 12, each said mainframe, 11, and/or said mechanically actuated lever, 12, having been positioned, on said mouthpiece, 13, so that it could be placed in its proper position in the interproximal area between two adjacent teeth, and said hardened material, 26, that holds said mainframes, 11, and/or said mechanically actuated levers, 12, together, as in FIG. 16. The proper position of said mouthpiece, 13, with respect to the dental arch is a position in which said mouthpiece, 13, is enabled to perform its intended tasks.

There are many ways of how to obtain at least one said mainframe, 11, and/or at least one said mechanically actuated lever, 12, properly placed in the mouths, which are connected to each other—if there is more than one said mainframe, 11, and/or said mechanically actuated lever, 12, and—to said hardened material, 26. One such way is that at least one said mainframe, 11, and/or at least one said mechanically actuated lever, 12, is connected to at least one said mainframe, 11, and/or at least one a mechanically actuated lever, 12—by a sort material, 26, before they are placed in the mouth. In this case, the dentist/hygienist inserts at least one mainframe, 11, and/or at least one mainframe said mechanically actuated lever, 12, together with said soft material, 26, that connects them together into the mouth of the patient and places said mainframes, 11, and/or at least said mechanically actuated levers, 12, in their proper position and then hardens said material, 26, or adds a layer of said material, 26, to the existing one in the mouth and then hardens said material, 26, so that each of said mainframes, 11, and/or said mechanically actuated levers, 12, retains its proper position with respect to the teeth and with respect to the rest of said mouthpiece, 13.

In another way to obtain at least one said mainframe, 11, and/or at least one said brushing units, 12, properly placed in said mouthpiece, 13, said mainframes, 11, and/or said brushing units, 12, are not connected to each other from the beginning. In a specific design of the invention, the dentist/hygienist first provides for said softened material, 26, on said lateral extension, 2, and then places one or more said mainframes, 11, and/or said mechanically actuated levers, 12, in their proper positions one at a time and hardens or allows to harden said material, 26, on each said mainframe, 11, and/or said mechanically actuated lever, 12, before placing another said mainframe, 11, or said mechanically actuated lever, 12. This ensures that the proper position of each said mainframe, 11, and/or said mechanically actuated lever, 12, is established because the impression of the teeth is imprinted on said material, 26, of said lateral extension, 2. In a specific design of the invention, the material, 26, placed on said lateral extension, 2, of one said mainframe, 11, or on said adjusting means, 25, of said mechanically actuated lever, 12, may overlap with said lateral extension, 2, of an adjacent said mainframe, 11, or said adjusting means, 25, of said mechanically actuated lever 12. One may also add said soft material, 26, to at least one said mainframe, 11, and/-or said mechanically actuated lever, 12, after one or more said mainframes, 11, and/or said mechanically actuated levers, 12, have been placed in their proper positions so as to connect one said mainframe, 11, or one said mechanically actuated lever, 12, with at least one said mainframe, 11, and/or one said mechanically actuated lever, 12, and harden said material, 26, or allow it to harden in order to impart strength and/or rigidity to said mouthpiece, 13.

The manipulation of tension on said flossing thread, 3, can bestow certain features to said mainframe, 11. As an example, if said flossing thread, 3, is loose to a degree, it can wrap around each individual tooth for more effective flossing, as in FIG. 5. Also the position of said flossing thread, 3, with respect to a specific tooth, influences the effectiveness of flossing. If one end of said flossing thread, 3, is close to a tooth, the effectiveness of flossing is enhanced at that side of the tooth to which an end of said flossing thread, 3, is close. While the effectiveness of flossing is diminished at that side of the tooth from which the end of said flossing thread, 3, is far. FIG. 12 shows said flossing thread , 3, wrapping around the tooth at that side of the tooth, which is close to one end of said flossing thread, 3, and thus effectively flossing the tooth, as opposed to the other side of the tooth, which is far from an end of said flossing thread, 3. These considerations prove important in the discussion of how said mouthpiece, 13, should be moved in the mouth to effectuate proper flossing.

Another example of a characteristic imparted by manipulating the tension on said flossing thread, 3, is to more easily guide said flossing thread, 3, into the area between two adjacent teeth by creating a tension on said flossing thread, 3. This is so because, firstly, said flossing thread, 3, having tension, is extended and straight. Therefore, when the patient intends to floss with a said mouthpiece, 13, he may place said mainframe, 11, along with said flossing thread, 3, anywhere in the space between the adjacent cusps of the two adjacent teeth for which space said mainframe, 11, has been designated, as in FIG. 14. However, if said flossing thread, 3, is too loose, it may reach over the cusp and be entangled by it. Even though the drawing in FIG. 14 shows two adjacent molar teeth, the tension on said flossing thread, 3, solves the problem of entanglement if the point of contact between two teeth involves one or two molars, premolars, canines, or incisors. Secondly, said flossing thread, 3, would more easily pass through a point of contact between two adjacent teeth if there is a tension on said flossing thread, 3. Furthermore, tension on said flossing thread, 3, can be used to find the proper place of said mouthpiece, 13, with respect to the patient's dental arch.

Figure 17:
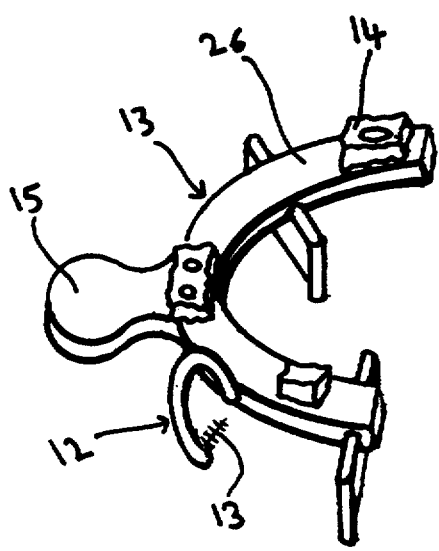
FIG. 17 illustrates a custom made mouthpiece containing impression of the opposite arch at different areas and a handle extending out of the mouth when the custom made mouthpiece is in its proper place on the dental arch.

In one specific design of the invention, the proper use of said mouthpiece, 13, is facilitated by the cooperation between the two dental arches. Therefore, the impression, 14, of the opposite arch is taken, preferably using an impression material. Said impression, 14, need neither be accurate nor cover the entire arch. A preferred method of incorporating said impression 14 on said mouthpiece 13 is as follows. With said cured impression, 14, attached to the arch and said mouthpiece, 13, placed in its proper position on the opposite arch, the patient closes his/her mouth preferably as much as possible, preferably in a slightly protrusive position— that is, in a patient with an Angle's class I occlusion—after some adhesive is placed between said mouthpiece, 13, and said impression, 14, thereby gluing them together. FIG. 17 shows said impression, 14, glued to said mouthpiece, 13. Of course, other means of connecting together said mouthpiece, 13, and said impression material, 14, are also possible.

In another specific design of the invention, a handle, 15, connected to said mouthpiece, 13, and extending out of the mouth when said mouthpiece, 13, is placed in the mouth, is provided, exclusively, or together with said impression, 14, of the opposite arch, as in FIG. 17. Said handle, 15, and/or said impression, 14, are utilized to effectuate and guide the movement of said mouthpiece, 13, said movement being necessary to effectively floss the teeth.

The features of the present invention include a gum massaging device, 10, incorporated in said mouthpiece, 13, as in FIG. 9. It can be provided as an option to the patient by the dentist/hygienist. Said gum massaging device, 10, is a means, preferably a flexible one, which is so connected to said mouthpiece, 13, as to rub against the gum when said mouthpiece, 13, is moved about after it is placed on the dental arch. Said gum massaging device, 10, may take one of many forms. For example, it could be a studded ribbon made of rubber that is connected to said mouthpiece, 13, in such a way that it can come in contact with the gum. A cross section view is provided in FIG. 9. As one moves said mouthpiece, 13, said gum massaging device, 10, rubs against the gum, and massages it. The advantages of having said gum massaging device, 10, mounted on said mouthpiece, 13, include saving time and effort to massage the gum. In a specific design of the invention, said gum massaging device, 10, is mounted on said mouthpiece, 13, in such a way that it massages the gum when the patient is using said mouthpiece, 13, to floss and/or brush his/her teeth. In another specific design of the invention, said gum massaging device, 10, is mounted on said mouthpiece, 13, in such a way that it massages the gums without causing said mouthpiece, 13, to floss and/or to brush the teeth. This situation is preferably effectuated by positioning said gum massaging device, 10, slightly more apical than those said mainframes, 11, or those said mechanically actuated levers, 12—that exist in said mouthpiece, 13—when said mouthpiece, 13, is placed on the dental arch.

In a specific design of the invention, during the construction of said mouthpiece, 13, a dentist/hygienist may place a flexible or bendable material such as a hinge 17 in said mouthpiece, 13, preferably in the anterior area of the arch, as in FIG. 11, in such a way that once said material, 26, is hardened, it will be easier to remove said mouthpiece, 13, from and reposition it in the mouth using said hinge, 17, or any such said flexible or bendable material which helps the patient bend said mouthpiece, 13, so that it could pass through the lips more easily, as in FIG. 11.

In a specific design of the invention, a spring, 18, can be provided between said mouthpiece, 13, and the hard and soft tissue of the same dental arch, as in FIG. 8. When said mouthpiece, 13, moves apically when it is placed on the dental arch—for example, by the patient closing the mouth when said custom made mouthpiece, 13, has said impression, 14, of the opposite arch, and/or by using said handle, 15, to move said custom made mouthpiece, 13, and said spring, 18, is compressed. When the patient relaxes his/her mouth, or opens it, and/or removes the pressure on said handle, 15, said spring, 18, between said custom made mouthpiece, 13, and tooth and/or living tissue pushes said custom made mouthpiece, 13, away from the tooth and/or the living tissue and said flossing thread, 3, moves coronally. In order not to harm the papilla, mesiodistal, distomesial, buccolingual, and linguobuccal movements of said flossing thread, 3, should preferably take place when said flossing thread, 3, is in a coronal position—just apical to the point of contact between teeth. Therefore, in this specific design, the above mentioned movements should preferably take place in an open mouth.

The proper position of said mainframe, 11, can constitute different positions. A preferred example of said position is placing all flossing threads, 3, towards the mesial of the papilla against the distal wall of the mesial adjacent tooth. In this example, said mainframe, 11, is pushed against said mesial adjacent tooth so that said flossing thread, 3, enters the sulcus and wraps around said tooth. The dentist/hygienist may keep said mainframe, 11, in this position until said soft material, 26, located on said lateral extension, 2, of said mainframe, 11, and/or on said adjusting means, 25, of said mechanically actuated lever, 12, is hardened. He may also add—as an alternative way or in conjunction to the method taught above—a layer of said soft material, 26, in order to adhere and/or keep in place said mainframe, 11, to the rest of said custom made mouthpiece, 13, and thereby fix the position of said mainframe, 11, with respect to the rest of said custom made mouthpiece, 13, by hardening said material, 26.

A main idea behind the design of said mechanically actuated lever, 12, is that said mechanically actuated lever, 12, should not interfere with the placement of said custom made mouthpiece, 13, in its proper place on a dental arch in order to use said custom made mouthpiece, 13. Only after the proper placement of said custom made mouthpiece, 13, a patient would like to actuate said mechanically actuated levers, 12, so that one said brush, 19, would enter the interproximal area of two adjacent teeth and clean it. A preferred way of actuating said mechanically actuated lever, 12, is accomplished by closing one's mouth. A preferred way of removing said brush, 19, from the interproximal area is by means of said spring, 20, returning said brush 19 its original position, i.e.: the one before actuation. This provides for easy removal of said custom made mouthpiece, 13, from the dental arch, since when said brush, 19, is extended into the interproximal area, the removal of said custom made mouthpiece, 13, out of the mouth is difficult or impossible.

A preferred way to place one or more said mechanically actuated levers, 12, in said custom made mouthpiece, 13, is accomplished at the time said custom made mouthpiece, 13, is constructed. In a specific design of the invention, for convenience, said mechanically actuated levers, 12, are provided in an extended position; i.e.: in the position which said mechanically actuated lever, 12, is in when the patient closes his/her mouth. In this position, said brush, 19, in said mechanically actuated lever, 12, once said mechanically actuated lever, 12, is in its proper position on the teeth, is extented maximally into the interproximal area. Once said mechanically actuated lever, 12, is in proper position on the teeth and said brush, 19, is extended maximally into the interproximal area, the dentist/hygienist connects said mechanically actuated lever, 12, to the rest of said custom made mouthpiece, 13, which is also properly placed on the teeth, using said soft material, 26. Once the construction of said custom made mouthpiece, 13, is completed, the dentist/hygienist releases said spring(s), 20—which were in a compressed form until now through the use of a retainer to keep said spring, 20, in a compressed state—and thereby pulls out said brush(es) 19 out of the interproximal area. Said retainer is removed after releasing said spring, 20.

Having described specific embodiments of this invention with reference to the accompanying drawings, it is to be understood that the invention is not limited to those precise embodiments, and that various changes and modifications may be affected therein by one skilled in the art without departing from the scope or spirit of the invention as defined only in the appended claims.

What is claimed is:

1. A custom made flossing mouthpiece used for flossing a plurality of interproximal areas together in a dental arch, said mouthpiece comprising:

a plurality of mainframes, each mainframe including at least one elongate member supporting at least two arms, said at least two arms projecting from said at least one member in generally the same direction, and a flossing thread retained by said at least two arms so that said thread is held in a position away from said at least one elongate member by a distance enabling flossing of teeth, and a mouthpiece member holding said mainframes in position, said mouthpiece member formed of a material having an initial soft state.

2. A mouthpiece according to claim 1, said mouthpiece further comprising a plurality of mechanically actuated levers, each of said levers comprising:

a pivot attached to said mouthpiece member, and at least one brush, said at least one brush capable of entering an interproximal area from generally a facial or lingual direction when said mouthpiece is positioned on the dental arch of a patient.

3. A mouthpiece according to claim 2, wherein said brushes held by said levers are replaceable.

4. A mouthpiece according to claim 2, wherein said mouthpiece comprises a flexible material, allowing bending of said mouthpiece to facilitate insertion and removal from a patient's mouth.

5. A mouthpiece according to claim 2, further including an impression of at least one portion of a user's jaw, said impression positioned on a side of said mouthpiece member in opposite relation to said mainframes, so that when said mouthpiece is placed in said user's mouth, said impression will conform to an area of one of said user's jaws.

6. A mouthpiece according to claim 2, wherein at least one of said arms of at least one of said mainframes further comprises a spring connecting said at least one said arm to said at least one mainframe so as to exert an outwardly directed force on said at least one said arm.

7. A mouthpiece according to claim 1, further comprising a plurality of receptacles, each of said;receptacles being held and attached to said member, each of said receptacles retaining a respective one of said mainframes, allowing said mainframes to be replaced.

8. A mouthpiece according to claim 1, wherein at least one of said mainframes has a flexible portion so that at least one of said arms of said at least one mainframe is moveable in outwardly and inwardly directions.

9. A mouthpiece according to claim 8, further comprising a spring attached to said at least one arm for exerting a pushing force on said at least one said arm.

10. A mouthpiece according to claim 9, wherein said at least one of said mainframes includes at least two blocking bodies which face each other, said bodies adapted to limit inwardly movement of said at least one arm.

11. A mouthpiece according to claim 1, wherein at least one of said mainframes further includes a lateral extension, at least part of said extension being formed of a material capable of being softened.

12. A mouthpiece according to claim 1, wherein said mouthpiece comprises a flexible material, allowing bending of said mouthpiece to facilitate insertion and removal from a user's mouth.

13. A mouthpiece according to claim 1, further including at least one handle projecting from said mouthpiece member, said handle adapted to extend out of a user's mouth when said mouthpiece is within said user's mouth.

14. A mouthpiece according to claim 1, further including an impression of at least one portion of a user's jaw said impression positioned on a side of said mouthpiece member in opposite relation to said mainframes, so that when said mouthpiece is placed in said user's mouth, said impression will conform to an area of one of said user's jaws.

15. A mouthpiece according to claim 2, further including at least one spring adapted to force said mouthpiece in a direction away from an arch on which said mouthpiece is located when in a user's mouth.

16. A mouthpiece according to claim 1, wherein at least one of said mainframes is flexible along at least a portion thereof, so that at least a portion of said at least one mainframe is rotatable with respect to another portion of said at least one mainframe.

17. A mouthpiece according to claim 16, wherein at least one of said arms of at least one of said mainframes further comprises a spring connecting said at least one said arm to said at least one mainframe so as to exert an outwardly directed force on said at least one said arm.

18. A mouthpiece according to claim 17, further including at least two blocking bodies, said bodies adapted to limit inward movement of said at least one arm with respect to said at least one mainframe.

* * * * *